United States Patent [19]
Kihara et al.

[11] Patent Number: 5,402,366
[45] Date of Patent: Mar. 28, 1995

[54] METHOD AND APPARATUS FOR SIMULATING A MECHANICAL OPERATION

[75] Inventors: Shigefumi Kihara; Akihiko Yoshii, both of Ehime, Japan

[73] Assignee: Sumitomo Heavy Industries, Ltd., Tokyo, Japan

[21] Appl. No.: 976,505

[22] Filed: Nov. 13, 1992

[30] Foreign Application Priority Data

Nov. 14, 1991 [JP] Japan .................. 3-299259

[51] Int. Cl.6 ............ G06F 15/60; G06F 15/62
[52] U.S. Cl. ................... 364/578; 364/476; 364/149; 364/505; 364/508; 73/826; 73/823; 73/804; 73/783
[58] Field of Search ............ 364/578, 476, 149, 505, 364/508; 228/121, 122, 120; 73/826, 799, 147, 823, 804, 783

[56] References Cited

U.S. PATENT DOCUMENTS

| | | | |
|---|---|---|---|
| 3,896,666 | 7/1975 | Johnson et al. | 73/147 |
| 4,567,774 | 2/1986 | Manahan et al. | 73/826 |
| 4,797,842 | 1/1989 | Nackman et al. | 364/578 |
| 4,844,323 | 7/1989 | Kondo et al. | 228/121 |
| 4,895,027 | 1/1990 | Manahan, Sr. | 73/799 |
| 4,933,889 | 6/1990 | Meshkat et al. | 364/578 |
| 5,136,497 | 8/1992 | Coe et al. | 364/578 |
| 5,202,837 | 4/1993 | Coe et al. | 364/476 |

OTHER PUBLICATIONS

"Finite Element Analysis On Elastoplasticity In Die Forging Of A Gear Material", *The Proceedings of the Japanese Spring Conference for the Technology of Plasticity*, by Manabu Goto et al. May 1989.

Primary Examiner—Emanuel T. Voeltz
Assistant Examiner—Alan Tran
Attorney, Agent, or Firm—Burns, Doane, Swecker & Mathis

[57] ABSTRACT

A method and apparatus for simulating a mechanical operation is based on the finite element method and uses a particle flow model. Evaluation of contact boundary between a die and a material and remeshing operation are unnecessary. Particles (6) are moved on fixed elements to change material properties therein. The elements per se are not deformed.

4 Claims, 16 Drawing Sheets

STROKE = 6.0 mm

STROKE = 12.0 mm

STROKE = 13.5 mm (REMESHING)
------ BEFORE REMESHING
———— AFTER REMESHING

STROKE = 15.0 mm (FINAL STATE)

BEFORE DEFORMATION    AFTER DEFORMATION

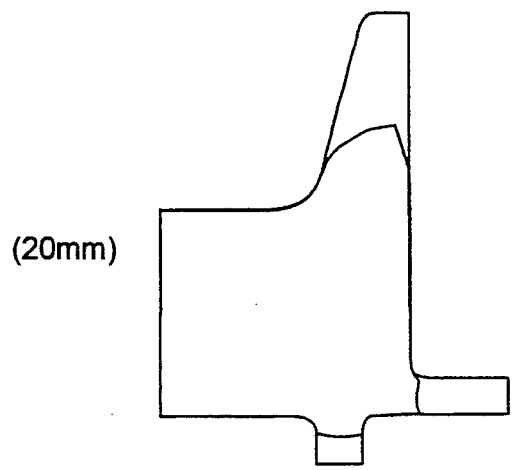 (20mm)
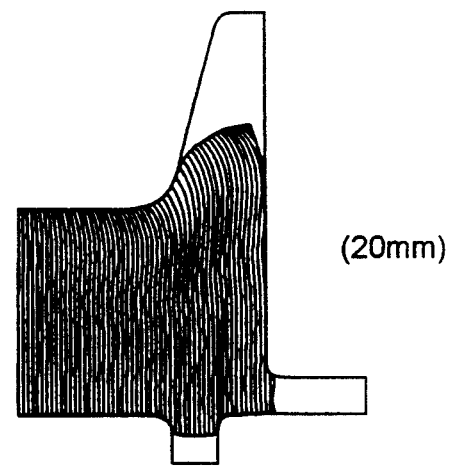 (20mm)
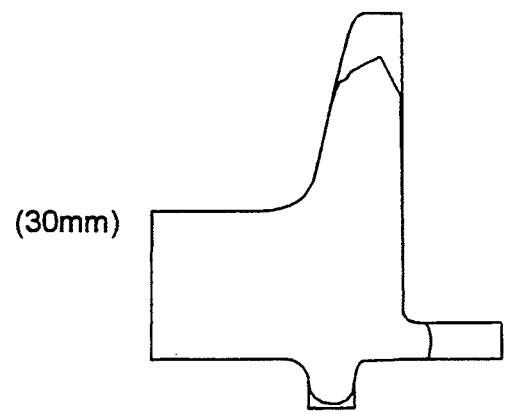 (30mm)
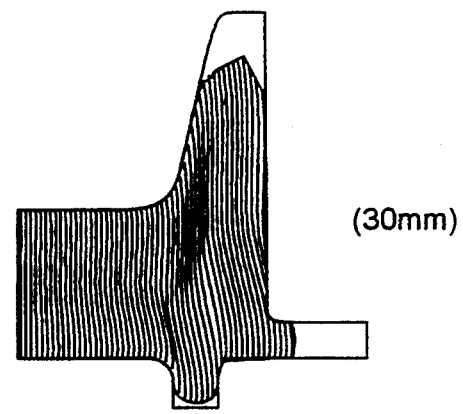 (30mm)
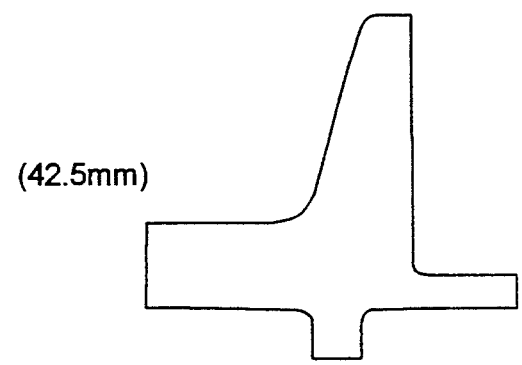 (42.5mm)
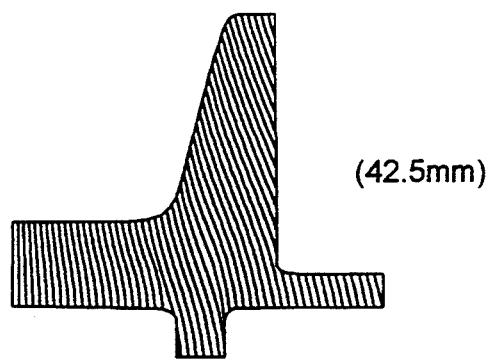 (42.5mm)
Fig. 14a      Fig. 14b

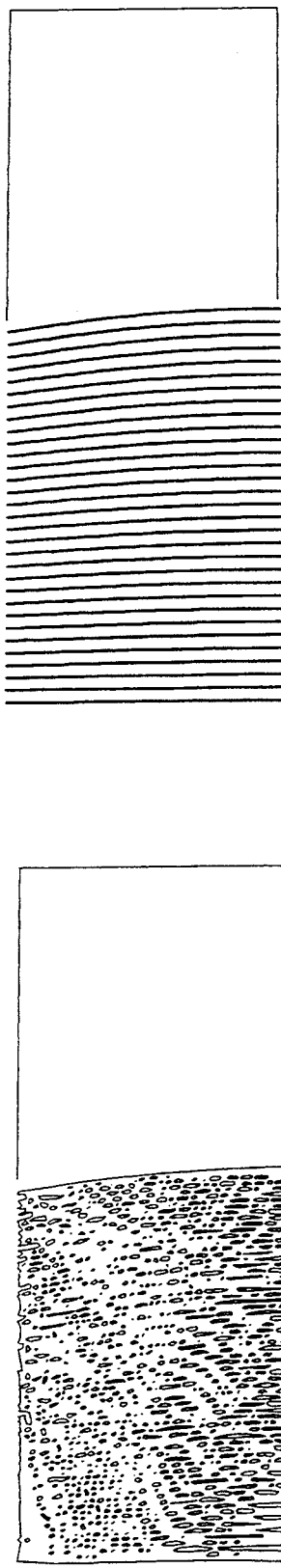
Fig. 20a REDUCTION RATE $\Delta H/H_O$=20%
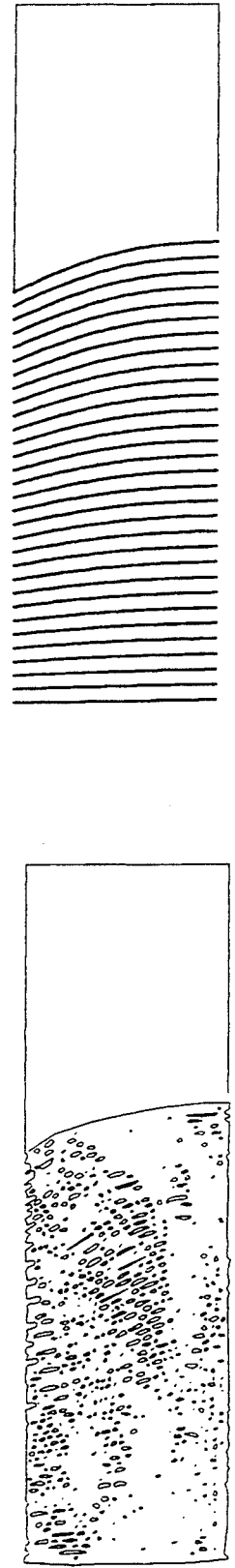
Fig. 20b REDUCTION RATE $\Delta H/H_O$=40%

METHOD AND APPARATUS FOR SIMULATING A MECHANICAL OPERATION

BACKGROUND OF THE INVENTION

This invention relates to a method and apparatus for simulating a mechanical operation and, in particular, to an operation in the forming industries.

In such molding industries, a shape of a material, a die and a manufacturing process must be carefully designed in order to improve a quality of a product and to reduce a cost.

Heretofore, ordinary simulation apparatuses have been used to analyze a flow and deformation process of a material for the purpose of prediction in product design. For example, a conventional analyzing method is disclosed in a paper written by Manabu Goto and Tomotsugu Shibuya and contributed to The Proceeding of the 1989 Japanese Spring Conference for the Technology of Plasticity under the title of "Finite Element Analysis on Elastoplasticity in Die Forging of a Gear Material". Specifically, let a product illustrated in FIG. 1 be deformed by the use of a die D and a material M illustrated in FIG. 2. The material M alone is divided or meshed into a plurality of divided elements or finite element meshes as shown in FIG. 2. Simulation is carried out by predicting changes of the divided elements which might occur during a forming operation. Results of the simulation is illustrated in FIGS. 3(a) through 3(d). In FIGS. 3(a) through 3(d), the die D is assumed to be moved from an initial state (FIG. 3(a)) to a final state (FIG. 3(d)) at strokes of 6.0 mm, 12.0 mm, 13.5 mm, and 15 mm, respectively. As is apparent from FIG. 3(c), re-division or remeshing should be done in connection with the divided elements, as depicted by solid lines. This means that the divided elements are undesirably deformed during the forming operation.

Specifically, the above-mentioned conventional method is carried out on the basis of a "finite element" program which includes an additional step in consideration of a predetermined boundary condition and remeshing. Thus, a basic forming operation is analyzed by the deformation finite elements by considering states before and after deformation, as shown in FIG. 4. In this event, a flow and deformation process of a material is numerically simulated in accordance with the finite element program by modelling the material alone of both the material and the die by the use of finite elements and by tracing the deformation of the finite elements themselves.

However, the conventional method should consider and evaluate a contact boundary between the die and the material as suggested in FIG. 5. This inevitably results in a calculation error because such evaluation of a contact is very difficult.

More particularly, the finite elements per se are deformed in the conventional method as mentioned above. With the progress of deformation, the finite elements are so extensively distorted or deformed as shown in FIG. 6. This makes further calculation impossible. In order to cope with such an excessive deformation, the above-mentioned remeshing should be repeated at every time when the excessive deformation takes place. However, the remeshing is extremely troublesome for a user.

SUMMARY OF THE INVENTION

It is therefore an object of this invention to provide a method and an apparatus for readily simulating a mechanical operation on the basis of a finite element method.

It is another object of this invention to provide a method and an apparatus of the type described, which dispenses with neither necessity of evaluation of a contact boundary between a die and a material nor remeshing operation.

According to this invention, a method for simulating a mechanical operation by monitoring a flow of a material within an analysis space comprises the steps of dividing said analysis space into a first analysis region filled with the material and a second analysis region free from the material, partitioning the analysis space into a plurality of divided elements over the first and the second analysis regions, distributing particles in the divided elements which are located in the first analysis region, and monitoring movement of the particles in the analysis space with reference to at least one predetermined material property of the material.

BRIEF DESCRIPTION OF THE DRAWING

FIGS. 14(a) and (b) show results of the analysis in the first experimental example with deformation states provided by particle representation and streamline representation, respectively;

FIGS. 20(a) and (b) show results of the analysis in the third experimental example;

DESCRIPTION OF THE PREFERRED EMBODIMENTS

Principle of the Invention

Figures 7A, 7B:
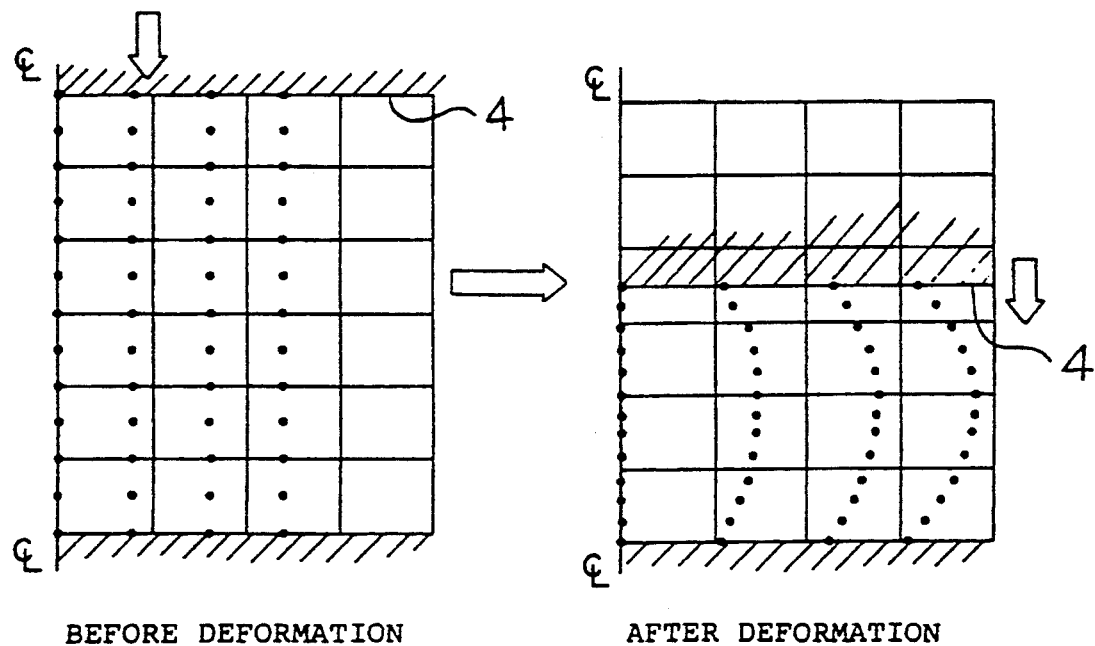
FIG. 7 is a view for describing operation of divided elements and particles according to this invention.

Referring to FIG. 7, a principle of this invention will be described for a better understanding of this invention. In FIG. 7, not only a material region filled with a material but also an empty region, namely, a non-material region including no material are contemplated for an analysis of a forming operation according to this invention as an analysis space. In this case, both the material region and the empty region are meshed or divided into elements which are kept unchanged during the forming operation, as readily understood from FIG. 7. In addition, particles are assigned to the material region, while no particle is assigned to each divided element, as shown in FIG. 7(a). Under the circumstances, deformation of the material is processed as the particle moving in the analysis space, as illustrated in FIG. 7(b).

With this principle, movement of the particles may be observed and analyzed in a manner to be described later in detail.

Embodiments

Figure 8:
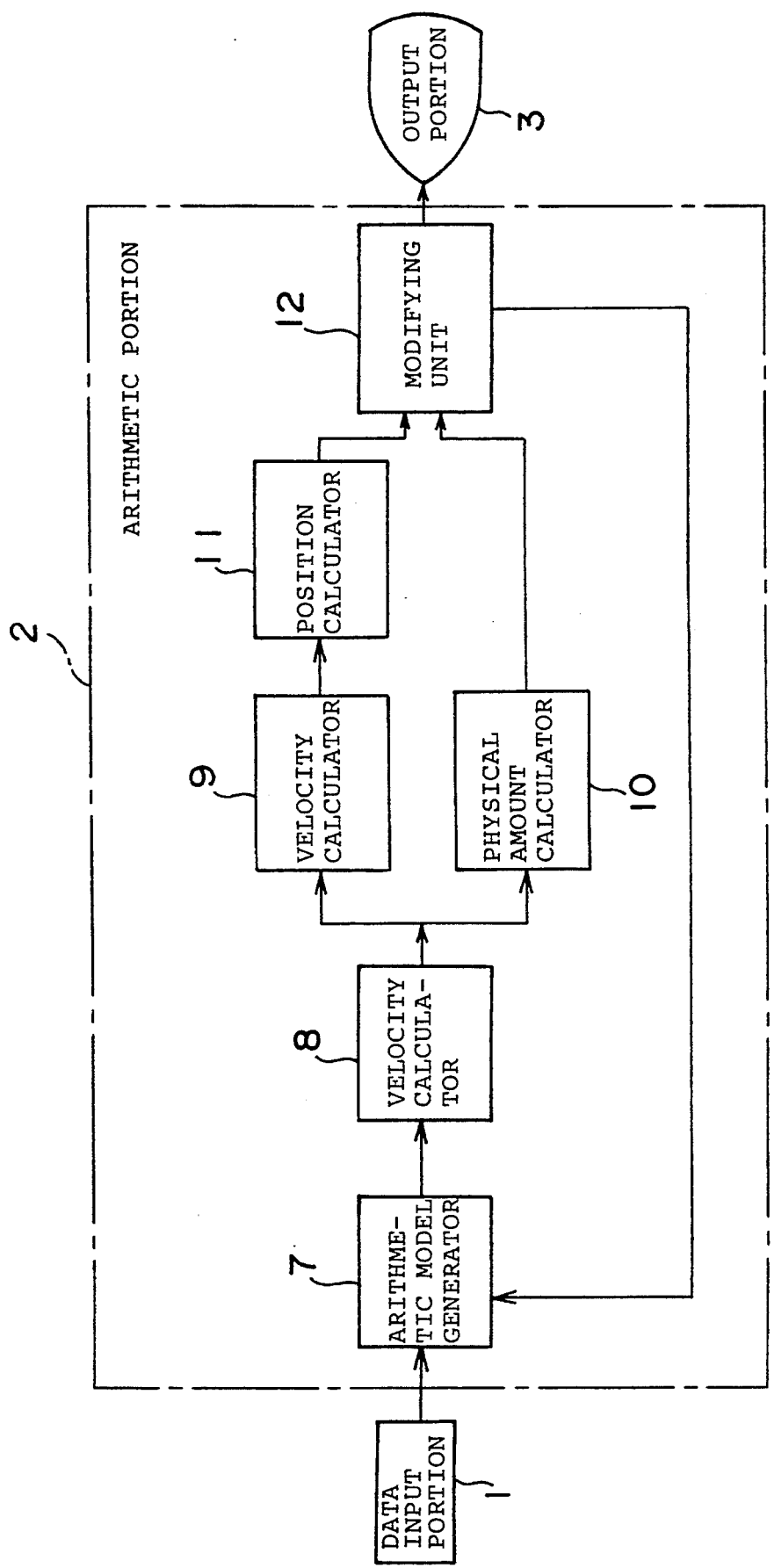
FIG. 8 is a block diagram of a simulation apparatus according to an embodiment of this invention.

Referring to FIG. 8, an apparatus for simulating a forming operation comprises a data input portion 1, an arithmetic portion 2, and an output portion 3. The data input portion is supplied with various data relating to a die and a material. By the use of the finite element method, the arithmetic portion 2 numerically simulates a flow and deformation process of the material on the assumption that the die is moved by a predetermined stroke. The result of simulation is delivered to the output portion 3.

Figure 1A:
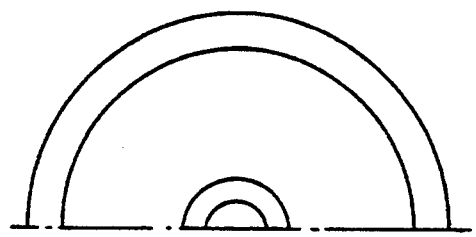
FIGS. 1(a) and (b) are views illustrating an example of a forming process subjected to a conventional finite element method.
Figure 1B:
Figure 2:
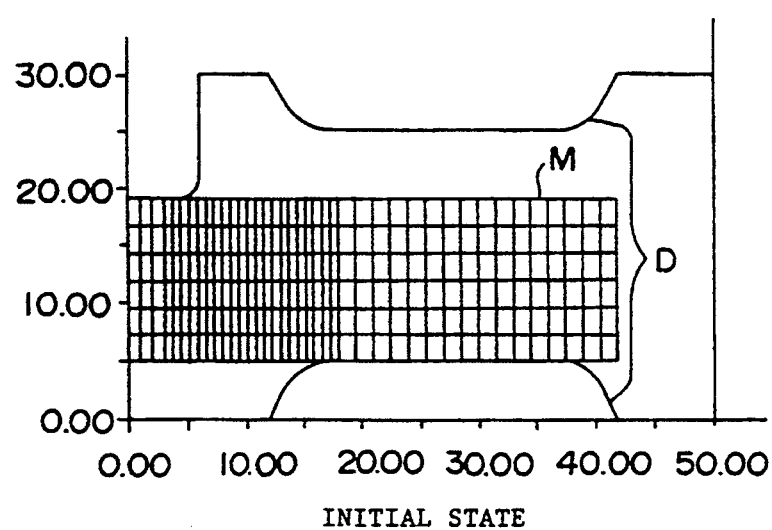
FIG. 2 is a view illustrating an example of a part of a die and a material divided into elements according to the conventional finite element method.
Figure 3A:
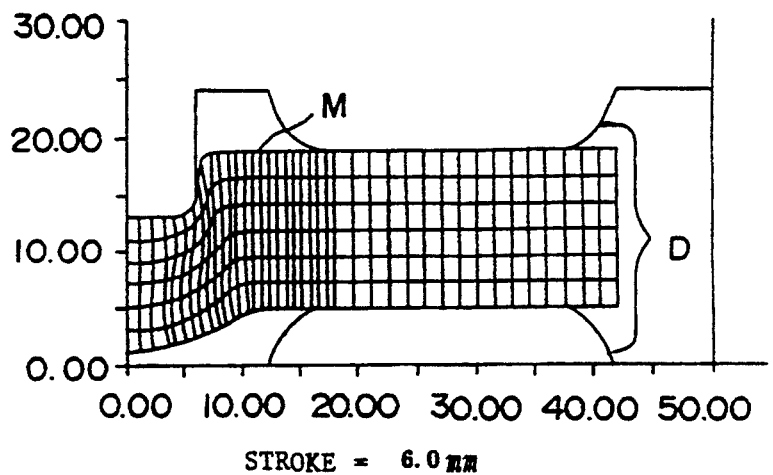
FIGS. 3(a) through (d) are views illustrating a die and a deformation process of the material divided into elements according to the conventional finite element method.
Figure 3B:
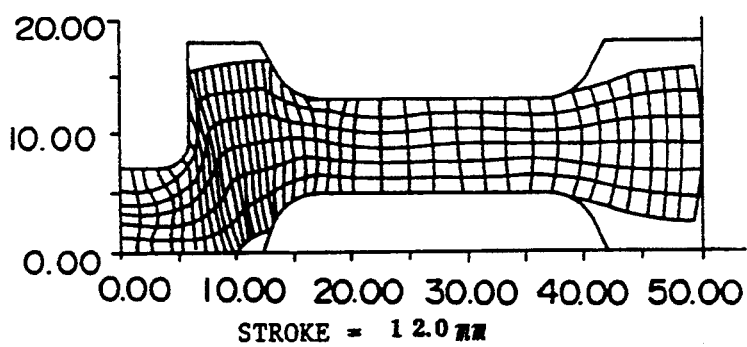
Figure 3C:
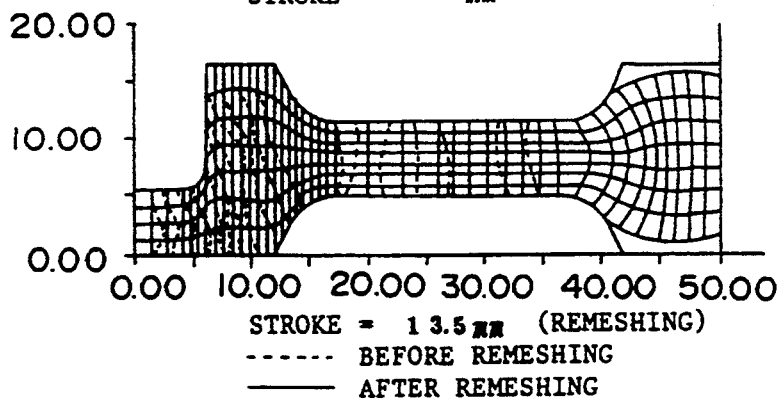
Figure 3D:
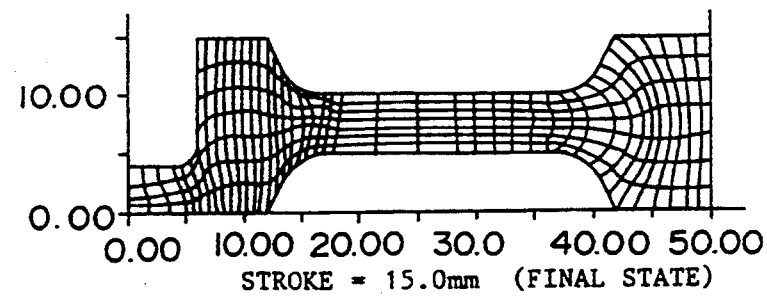
Figure 4:
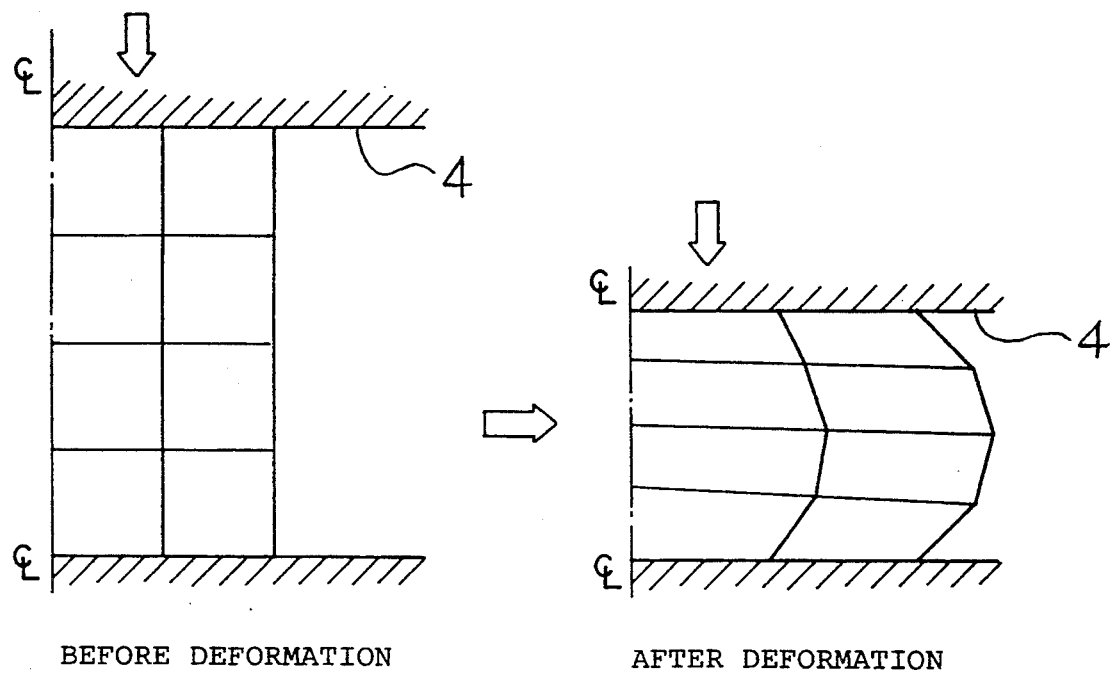
FIG. 4 is a view illustrating a die forging operation according to the conventional finite element method.
Figure 5:
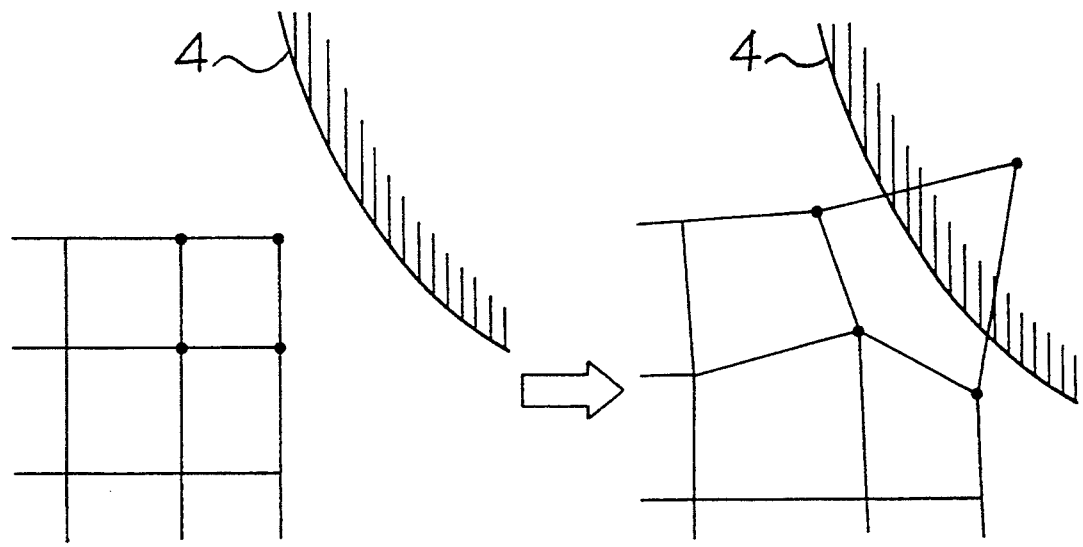
FIG. 5 is a view illustrating an evaluation of contact boundary between the die and the material in the conventional finite element method.
Figure 6:
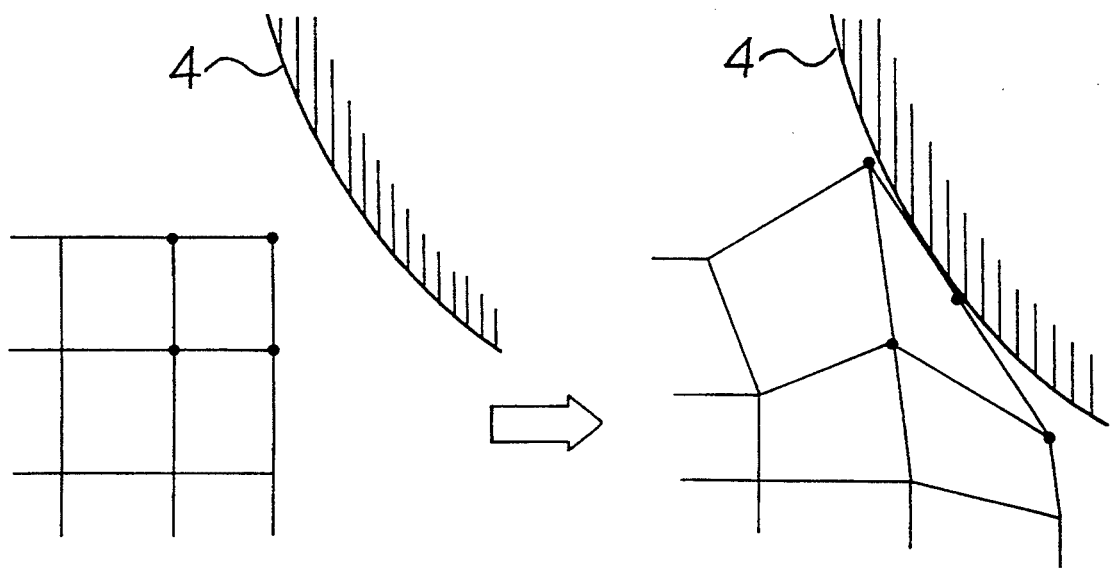
FIG. 6 is a view illustrating distortion of finite elements in the conventional finite element method.
Figure 9:
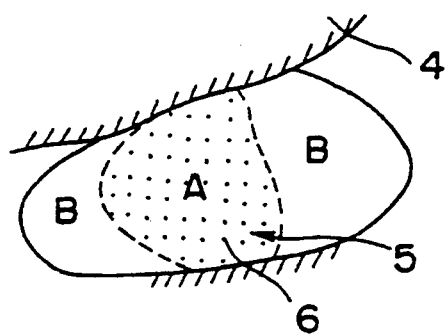
FIG. 9 is a view for describing an analysis region according to the embodiment of this invention.

Referring to FIG. 9 in addition to FIG. 8, operation of the apparatus will be described.

The arithmetic portion 2 comprises an arithmetic model generator 7, a velocity field calculator 8, a velocity calculator 9, a physical value calculator 10, a position calculator 11, and a modifying unit 12 for modifying material properties and physical values. The arithmetic portion 2 is implemented by hardware, such as a central processing unit (CPU).

Supplied with the input data, the arithmetic model generator 7 determines a whole analysis space which is defined within a die 4. The analysis space comprises a first analysis region A occupied by a material 5 and a second analysis region B where the material 5 is not present. Both the first and the second analysis regions are subjected to an analysis.

In FIG. 8, the arithmetic model generator 7 divides the first and the second analysis regions into a plurality of divided elements which may be fixed or semi-fixed. As shown in FIG. 9, particles 6 are distributed in the first analysis region A and are specified by position information in the material 5. Thus, an arithmetic model is created by forming a finite element model.

It is assumed here that the first and the second analysis regions A and B have first and second energy dissipation rates $\Phi_a$ and $\Phi_b$, respectively, which are different from each other. A total energy dissipation rate $\Phi$ of the whole analysis region is represented by the following Equation (1).

The first energy dissipation rate $\Phi_a$ of the first analysis region A comprises a first-part energy dissipation rate $\Phi_v$ due to plastic deformation of the material and a second-part energy dissipation rate $\Phi_s$ due to friction between surfaces of the material 5 and the die 4. When a dynamic energy dissipation rate takes a minimum value in a kinematically admissible velocity field, the exact velocity field is obtained.

$$\Phi = \Phi_a + \Phi_b \qquad (1)$$
$$= (\Phi_v + \Phi_s)_a + \Phi_b.$$

Equation (1) is rewritten into:

$$\Phi = (\int \bar{\sigma} \dot{\xi} dV + \int_s r \Delta u dS)_a + \Phi_b \; (\Phi_b \approx 0), \qquad (2)$$

where $\bar{\sigma}$ represents an equivalent stress, $\dot{\xi}$, an equivalent strain rate, r, a shear stress on a friction surface, namely, a friction shearing stress, $\Delta u$, a relative surface velocity between a tool and the material (particles), V, a volume of the material (particles), S, a contact area between that tool and the material (particles).

In practice, an infinitesimal value is given as the second energy dissipation rate $\Phi_b$ of the second analysis region B and is not greater than $\Phi_a$. This applies to the second analysis region B which is gradually occupied by the die 4 except for the empty region B. Stress is directly calculated from the strain rate components by introducing slight compressibility of the material.

Figure 10:
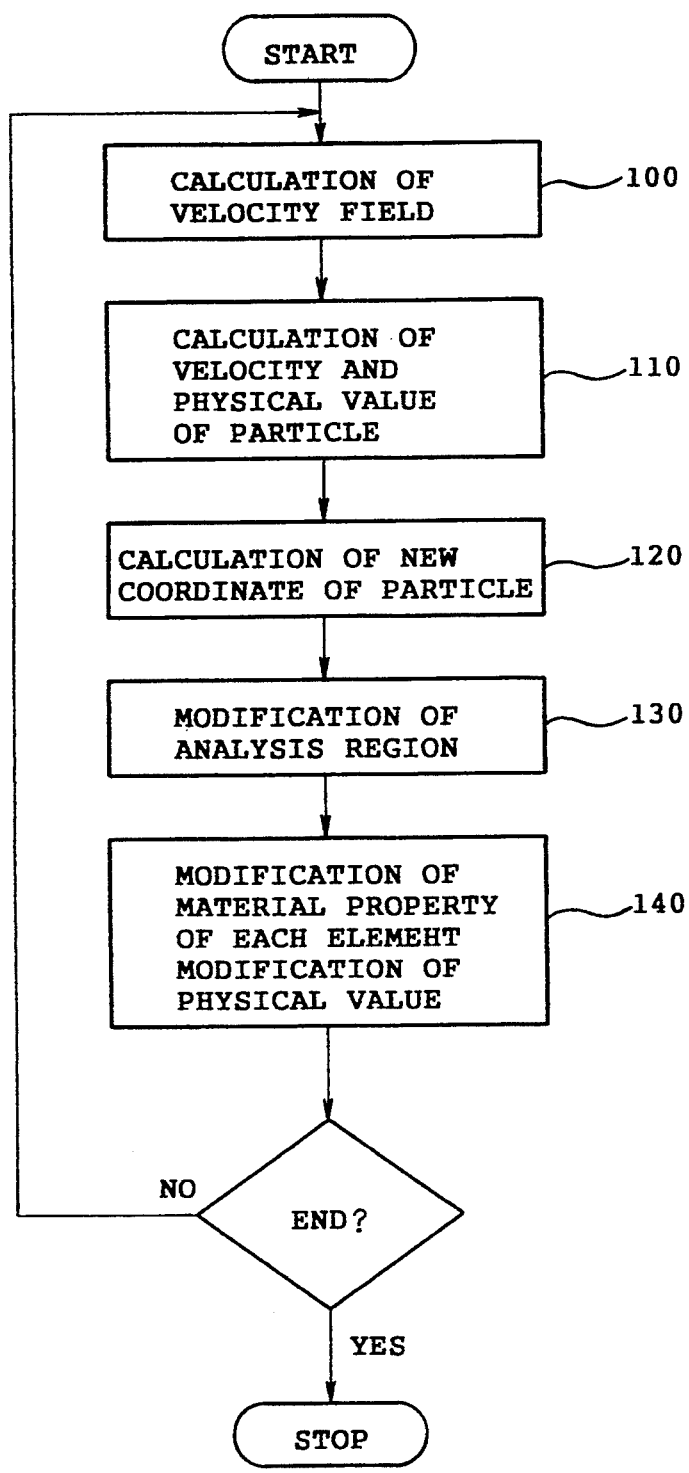
FIG. 10 is a flow chart in case when the analysis region according to the embodiment of this invention is moved along a predetermined direction.
Figure 11:
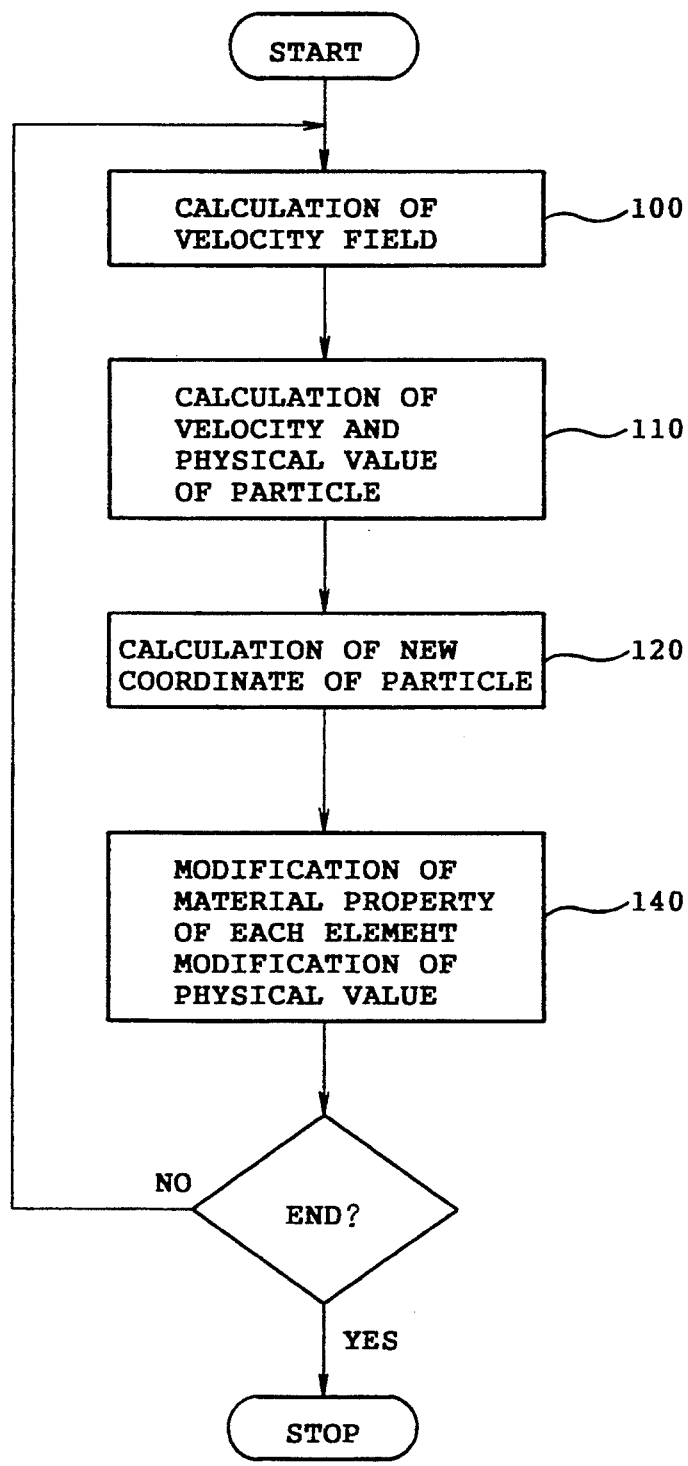
FIG. 11 is a flow chart in case when the analysis region according to the embodiment of this invention is completely fixed.

Next, operation of the arithmetic portion 2 will be described in detail referring to FIGS. 10 and 11.

The arithmetic portion 2 (FIG. 8) is for numerically simulating a flow and deformation process of the material by the use of the finite element method with reference to the changes of the physical values of the divided elements. The changes are caused to occur by the movement of the particles assigned to the divided elements.

The velocity field calculator 8 forms a finite element model by discretizing the whole analysis space into a plurality of divided elements each of which has four nodes and by assigning the particle or particles in each divided element. The velocity field calculator 8 calculates a velocity field in the while analysis space with reference to the die 4 and the material 5 so that the total energy dissipation rate $\Phi$ of the whole analysis space has a minimum value under a predetermined boundary condition.

The velocity field is given by a nodal velocity $u_a$ of each divided element in the first analysis region A to which the particles are assigned and a nodal velocity $u_b$ of each divided element in the second analysis region B to which no particle is assigned (Step 100).

The total energy dissipation rate $\Phi$ of the whole analysis space is represented as a function of the nodal velocities and is given by:

$$\Phi = \Phi(u1_a, u1_b),$$

$$u1_a = \{u_1, v_1, u_2, v_2, \ldots, u_n, v_n\}_a, \text{ and}$$

$$u1_b = \{u_1, v_1, u_2, v_2, \ldots, u_m, v_m\}_b, \quad (3)$$

where n represents the number of the nodes within the region of the particles, m, the number of the nodes within the region of no particle. The total number N (=n+m) of the nodes is kept constant during the simulation.

However, it is to be noted that each of the numbers m and n is changed from time to time with the movement of the particles.

The velocity calculator 9 acts to calculate a moving velocity of the particles by the use of an interpolation function Nj according to the following Equation (4) (Step 110). The exemplified interpolation function may be called a shape function.

$$\{u1_p\} = [Nj]\{u1_i\}$$

$$\{u1_p\} = \{u_{pk}, v_{pk}\} \text{ (k takes a selected one of 1 through the particle number)}$$

$$\{u1_i\} = \{u_{i1}, v_{i1}, u_{i2}, v_{i2}, \ldots, u_{il}, v_{il}\}$$

$$Nj = N(\xi, \eta), \quad (4)$$

where i=1 through n.

The shape function Nj is calculated by the following Equation (5) by the use of a coordinate $\{X_i\}$ of each node of the divided elements i and a coordinate $\{X_p\}$ of each particle. Since Equation (5) is given by a quadratic polynomial, the shape function Nj is practically calculated by the use of the Newton-Raphson method, as known in the art. Namely, $$\{X_p\} = [Nj]\{X_i\}. \quad (5)$$

Herein:

$$\{X_p\} = \{x_{pk}, y_{pk}\} \text{ (k takes a selected one of 1 through the particle number)}$$

$$\{X_i\} = \{X_{i1}, y_{i1}, x_{i2}, y_{i2}, \ldots, x_{il}, y_{il}\}.$$

At any rate, the moving velocity is calculated at every one of the particles by the velocity calculator 9.

The physical value calculator 10 calculates physical values of the divided elements with reference to the velocity field calculated by the velocity field calculator 8 (Step 110) in parallel with calculation of the moving velocities. Thus, each particle is defined by various information including a velocity, a strain, a strain rate, and a stress which may be referred to as data values. The above-mentioned data values at a particular one of the particles are represented by $\xi_p$, $\dot{\xi}_p$, and $\sigma_p$ and are calculated by the following formulae (6) in the manner similar to Equation (4).

$$\{\xi_p\} = [Nj]\{\xi_i\}$$

$$\{\dot{\xi}_p\} = [Nj]\{\dot{\xi}_i\}$$

$$\{\sigma_p\} = [Nj]\{\sigma_i\} \quad (6)$$

With reference to the moving velocity calculated by the velocity calculator 9, the position calculator 11 calculates a posterior position of the particles at which the particular particle is located after movement (Step 120). Namely, a coordinate of the posterior position after movement is calculated by the following Equation (7) by the use of the moving velocity of the particle obtained by Equation (4) and a time increment $\Delta t$.

$$\{X_p\}_N = \{X_p\}_o + \{u1_p\} \cdot \Delta t, \quad (7)$$

where $\{X_p\}_N$ and $\{X_p\}_o$ represent coordinates of the particle after movement and before movement, respectively.

In FIG. 8, the modifying unit 12 serves to modify material properties and physical values. Practically, the illustrated modifying unit 12 modifies the whole analysis regions along a movement direction of the die 4 (Step 130). The analysis regions are easily modified in consideration of a proportional movement along the movement direction of the die 4, as readily understood from FIG. 7. On the other hand, when the analysis regions are completely fixed, the operation of Step 130 is unnecessary as shown in FIG. 11.

The modifying unit 12 also carries out modification of the data values by feeding new physical values of the divided elements and new coordinates of the particles back to the arithmetic model generator 7 (Step 140), as illustrated in FIG. 8.

The analysis is completed after repeating the above-mentioned operation.

Experimental examples will hereinafter be described when a forging operation is analyzed according to this embodiment.

First Example

Figure 12:
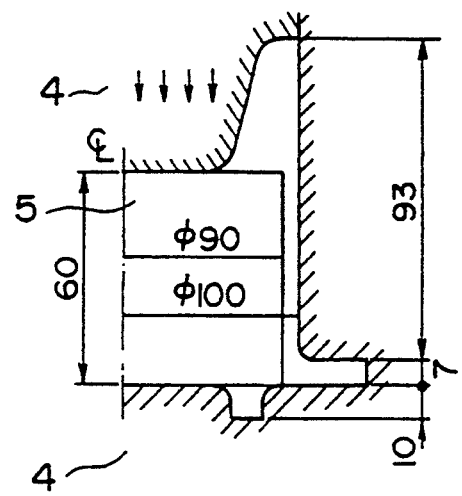
FIG. 12 is a view for use in describing a first experimental example of analyzing a forging operation.
Figure 13:
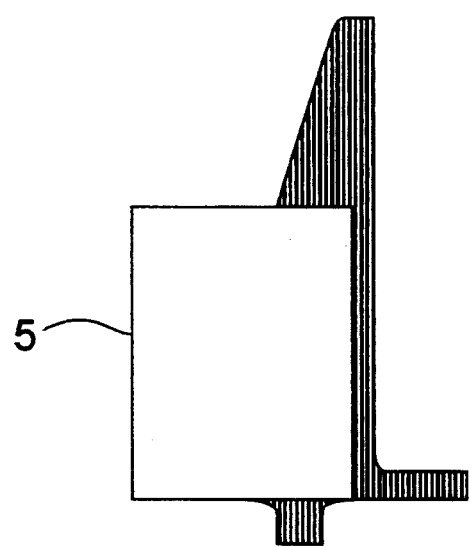
FIG. 13 shows divided elements in the first experimental example.

Referring to FIG. 12, the analysis is carried out in the above-mentioned manner as regards a die which has an axisymmetric structure and an inner diameter of 100 mm. In the illustrated example, it is assumed that the die 4 serves to reduce a stroke along a center axis from 42.5 mm to 17.5 mm. On the other hand, a cylindrical material 5 is assumed to have a diameter of 90 mm and a height of 60 mm. In FIG. 13, a ½ model alone is used in consideration of the axisymmetric structure and is divided into the elements which are equal in number to 1781. As shown in FIG. 13, the whole analysis space is defined not only in the material 5 but also in an empty space of the die 4 and is partitioned into divided elements. Although the material 5 looks like a black portion in FIG. 13 for convenience of illustration, the particles are distributed in the material 5. Thus, a particle representation is made in connection with the material 5. Under the circumstances, it is assumed here that the material 5 has the stress which is equal to $152\xi^{0.264}$ (Mpa) and which corresponds to that of pure aluminum, and the friction coefficient $\mu$ of 0.2.

FIGS. 14(a) and (b) show the states of deformation which are obtained by the analysis and which are specified by the particle representation and streamline representation, respectively. In any event, the material 5 is entered into the die 4 by strokes of 20 mm, 30 mm, and 42.5 mm in FIGS. 14(1), (2), and (3). With the movement of the die 4, the particles are moved and the die 4 is filled with the material 5.

Second Example

Next, description will be made about an analysis of a shearing operation hereinunder. Although a conventional thought is that the shearing operation is not suitable for the finite element method, such a shearing operation can be analyzed in accordance with this invention, as will become clear later.

Figure 15:
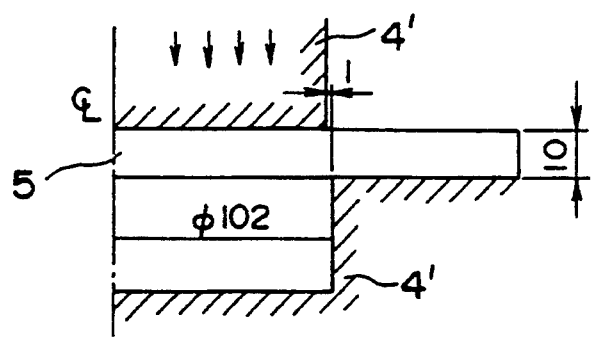
FIG. 15 is a view for use in describing a second experimental example of analyzing a shearing operation.

Referring to FIG. 15, it is presumed that a disk block has a thickness of 10 mm and a diameter of 190 mm and is cut or punched out by upper and lower blades 4' spaced by a gap of 1 mm to produce a disc having a diameter of 100 mm.

Figure 16:
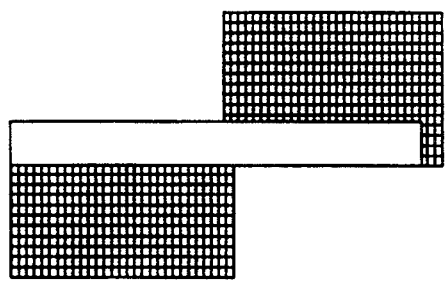
FIG. 16 shows divided elements in the second experimental example.

In FIG. 16, an analysis space is divided into the elements of 1296 in number with particles distributed in the disc block. The disc block has a material property $\sigma = 152 \xi^{0.264}$ (Mpa) which corresponds to that of the pure aluminum.

Figures 17A, 17B:
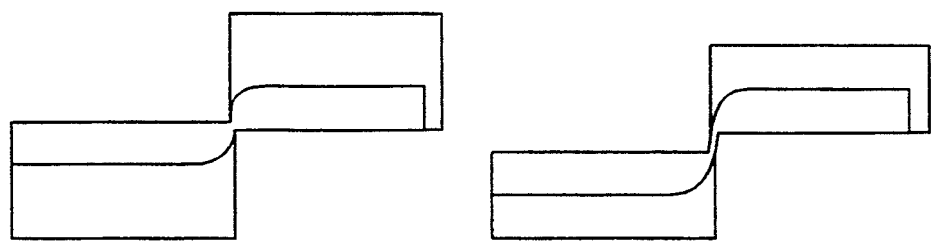
FIGS. 17(a) and (b) show results of the analysis in the second experimental example in the course of the shearing operation and upon completion of the shearing operation, respectively.

The results of the analysis are shown in FIGS. 17(a) and (b). FIG. 17(a) shows the status in the course of the shearing operation while FIG. 17(b) shows the status upon completion of the shearing operation. It is therefore understood from FIGS. 17(a) and (b) that the analysis of the shearing operation is also possible in accordance with this method from a start to a finish.

Third Example

Next, another experimental example of the analysis will be described in connection with a forming operation of upsetting a cylindrical material 5.

Figure 18:
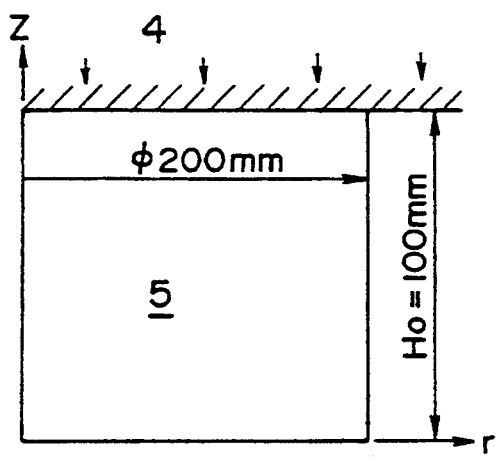
FIG. 18 is a view for use in describing a third experimental example of analyzing a molding operation of a cylindrical material or billet.

Referring to FIG. 18, let the cylindrical material 5 have a diameter D of 200 mm and a height 2Ho of 200 mm and be upset into a height of 120 mm.

Figure 19:
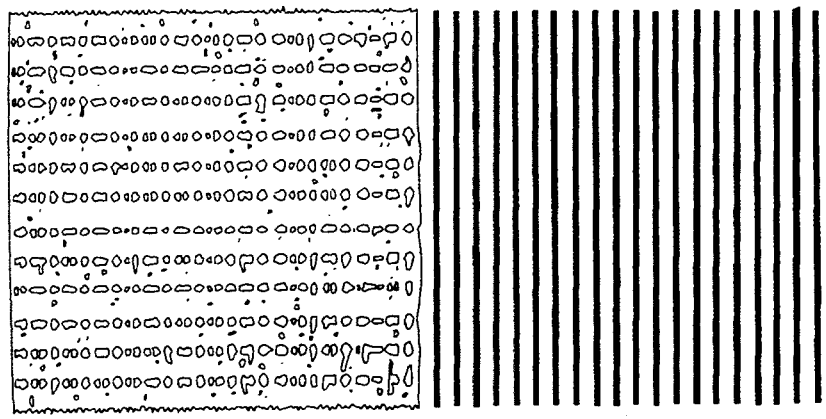
FIG. 19 shows divided elements in the third experimental example.

In FIG. 19, a ¼ model is used in consideration of a symmetrical structure and is divided into the elements. In the illustrated example, the analysis space has the first and the second analysis regions each of which is divided into the elements of 400 in number. As a result, a total number of the divided elements is equal in number to 800 (=20×40). Like in the above, the particles are assigned to the first analysis region and the material property $\sigma$ is equal to $152 \xi^{0.264}$ (Mpa) which corresponds to that of the pure aluminum. The friction coefficient $\mu$ is also assumed to be equal to 0.2.

In FIGS. 20(a) and (b), the material is deformed for the analysis according to this invention. In FIG. 20(a), an amount $\Delta H$ of reduction is equal to 20 mm, which shows a reduction rate $\Delta H/Ho$ of 20%. In FIG. 20(b), an amount $\Delta H$ of reduction is equal to 40 mm, which shows a reduction rate $\Delta H/Ho$ of 40%. The righthand figures provide streamline representations while the lefthand figures provide particle representations.

With the movement of the die 4, the particles are moved towards a periphery while the material is being deformed. Thus, the deformation of the material is clearly understood and analyzed by monitoring movement of the particles assigned to the first analysis region.

Figure 21A:
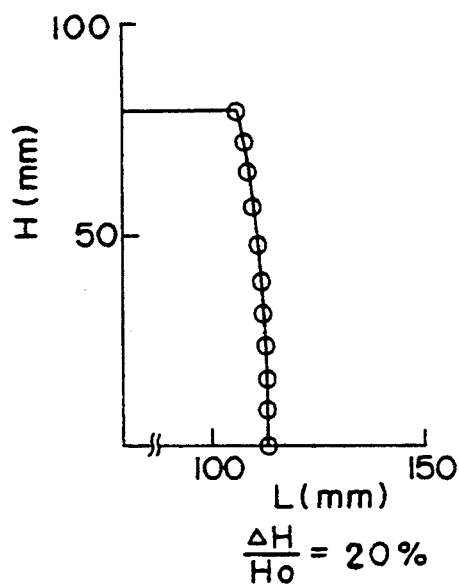
FIGS. 21(a) and (b) shows profiles of deformation of the cylindrical material in the third experimental example.
Figure 21B:
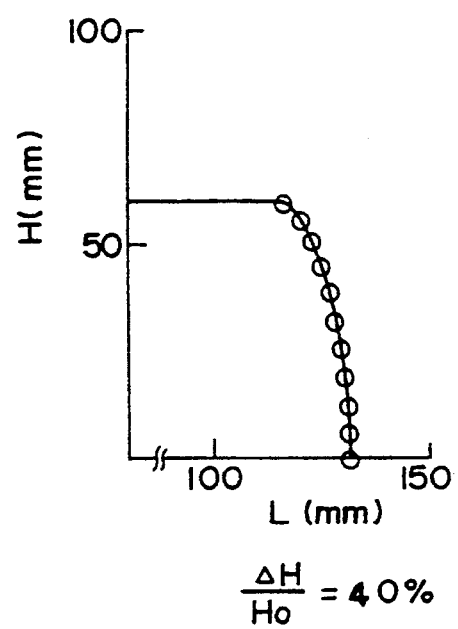

In FIGS. 21(a) and (b), the deformed profile of the billet is plotted. The plots are completely coincident with the comparative results depicted by circles and obtained by the rippls-forge operation (Discussion on J. Japan Soc. Tech. Plasticity by Osakada et al, 1984-10, p. 41).

Fourth Example

Figure 22:
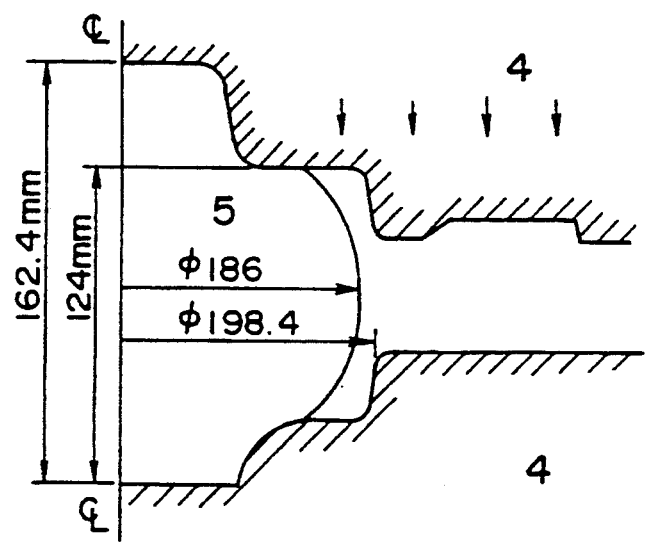
FIG. 22 is a view for describing a fourth experimental example of analyzing a forging operation of an axisymmetrical structure.

Referring to FIG. 22, the analysis is made about a forging operation of forging a material of an axisymmetrical configuration.

Figure 23:
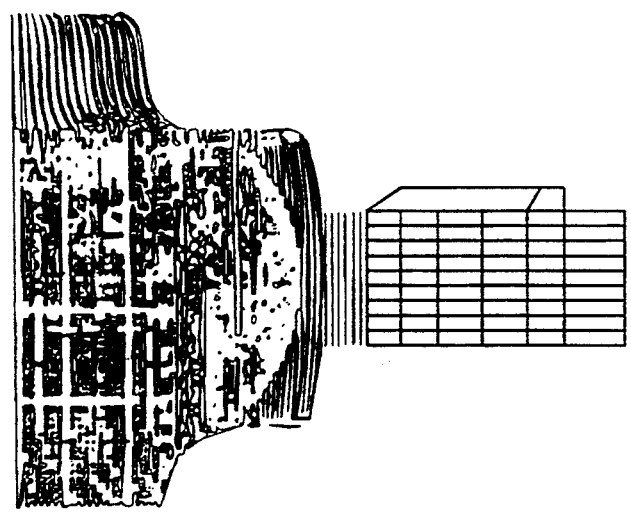
FIG. 23 shows divided elements in the fourth experimental example.

FIG. 23 shows a status of the divided elements. A ½ model is used in consideration of the symmetrical structure. The material has the material property $\sigma$ of $152 \xi^{0.264}$ (Mpa) and the friction coefficient $\mu$ of 0.2.

Figures 24A, 24B:
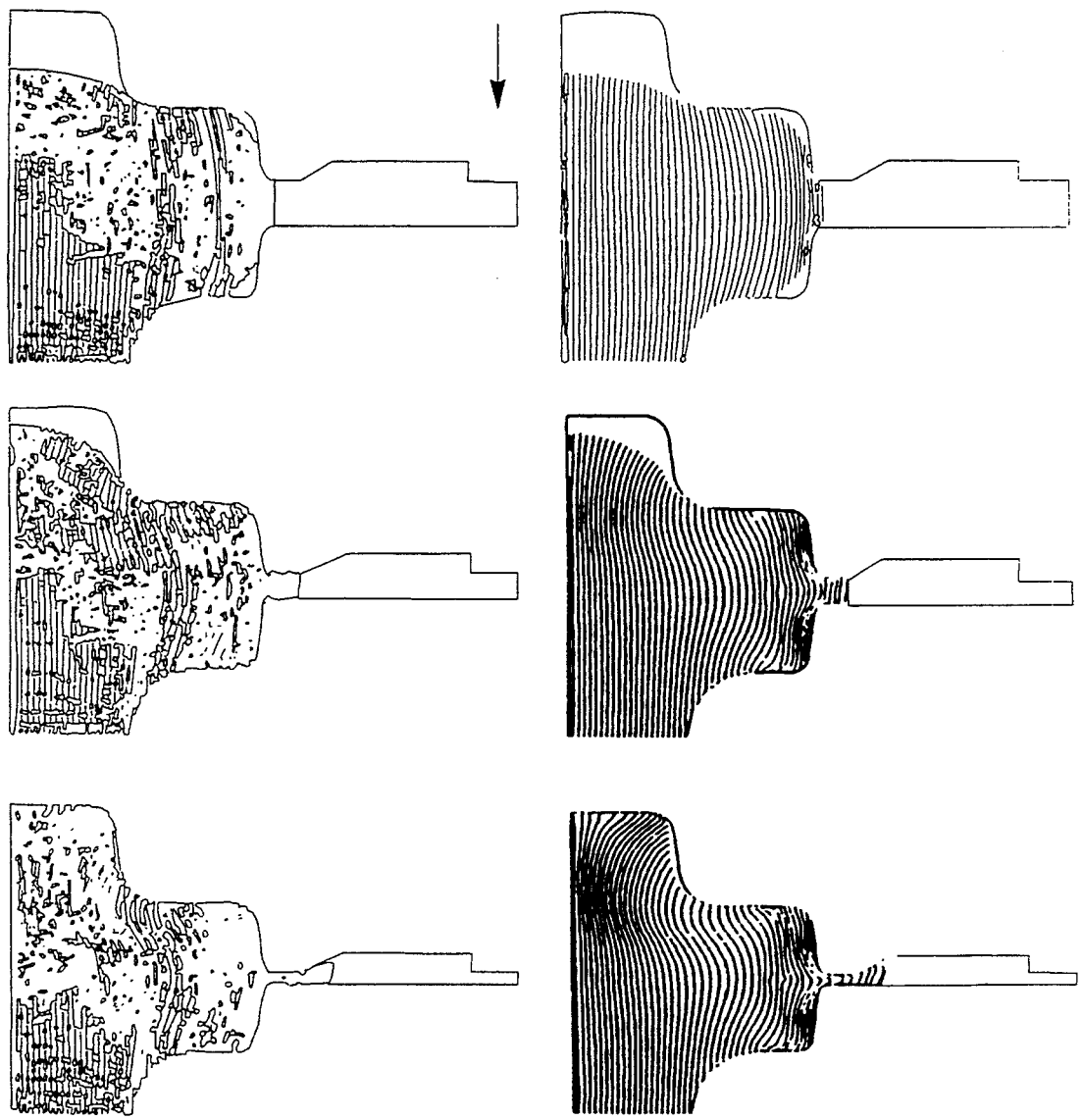
FIGS. 24(a) and (b) show results of the analysis in the fourth experimental example.

FIGS. 24(a) and (b) show a deformation process from the initial state to the final state in the form of particle and streamline representations, respectively. With the progress of deformation, the particles are brought into contact with the die 4 and the material 5 is filled in the die 4.

In the foregoing embodiments, this invention is described with reference to the apparatus for simulating a forging operation. However, this invention is also applicable to an injection molding machine.

As thus far been described, the deformation of the material is represented by the particle flow model according to this invention. Therefore, it is possible to carry out the analysis of the forging operation of a complicated structure without considering contact between the die and the material. In addition, remeshing operation is unnecessary.

What is claimed is:

1. A method for simulating a mechanical operation by monitoring a flow of a deformable material, said method comprising the steps of:

initially defining an analysis space which includes a first analysis region filled with said material and a second analysis region free from said material;

dividing said analysis space into a plurality of divided elements over said first and said second analysis regions;

distributing particles in said divided elements which are located in said first analysis region; and monitoring movement of said particles in said analysis space with reference to at least one predetermined material property of said material, said analysis space being kept unchanged while said first and said second analysis regions are changed with time.

2. A method for simulating a mechanical operation as claimed in claim 1, wherein the simulation is carried out by the use of a finite element method with reference to change of physical values of said divided elements, said change being caused by displacement of said particles moved on said divided elements.

3. An apparatus for simulating a mechanical operation by a die and numerically simulating a flow and deformation process of a deformable material molded by movement of said die using the finite element method, comprising:

an arithmetic model generator for defining an analysis space which includes a first analysis region occupied by said material and a second analysis region where said material is not present, modelling said first and said second analysis regions into finite element models, and distributing particles in said first analysis region to represent a shape of said material;

a velocity field calculator for calculating a velocity field in said analysis space in accordance with said die and said material so that energy dissipation in said analysis space has a minimum value under a predetermined boundary condition, said velocity field being given by a first nodal velocity of said divided elements in said first analysis region where said particles are present and a second nodal velocity of said divided elements in said second analysis region where said particles are not present;

a velocity calculator for calculating a moving velocity of said particles from said velocity field;

a position calculator responsive to said moving velocity calculated by said velocity calculator for calculating position information of said particles after being moved; and a physical value calculator responsive to said velocity field for calculating physical values of said divided elements.

4. An apparatus for simulating a mechanical operation by monitoring a flow of a deformable material within a defined analysis space, said material having a predetermined material property, said apparatus comprising:

dividing means for dividing said analysis space into a first analysis region filled with said material and a second analysis region free from said material;

dividing means for dividing said analysis space into a plurality of elements over said first and said second analysis regions;

distributing means for distributing particles in the divided elements which are located in said first analysis region; and monitoring means for monitoring movement of said particles in said analysis space with reference to said predetermined property of said material.

* * * * *